US00PP16399P3

(12) United States Plant Patent
Ellis et al.

(10) Patent No.: US PP16,399 P3
(45) Date of Patent: Apr. 4, 2006

(54) GRAPE PLANT NAMED 'G1-6819'

(50) Latin Name: ***Vitis* sp.**
Varietal Denomination: G1-6819

(75) Inventors: Philipus J. L. Ellis, Stellenbosch (ZA); Phyllis Burger, Stellenbosch (ZA)

(73) Assignee: Agricultural Research Council, Stellenbosch (ZA)

( * ) Notice: Subject to any disclaimer, the term of this patent is extended or adjusted under 35 U.S.C. 154(b) by 156 days.

(21) Appl. No.: 10/857,045

(22) Filed: May 28, 2004

(65) Prior Publication Data

US 2005/0039236 P1 Feb. 17, 2005

(30) Foreign Application Priority Data

Jun. 1, 2003 (ZA) ..... PT 3838

(51) Int. Cl.
*A01H 5/00* (2006.01)

(52) U.S. Cl. ..... Plt./207

(58) Field of Classification Search ..... Plt./207, Plt./205

See application file for complete search history.

*Primary Examiner*—Anne Marie Grunberg
*Assistant Examiner*—June Hwu
(74) *Attorney, Agent, or Firm*—Christie, Parker & Hale, LLP

(57) ABSTRACT

A new and distinct variety of Grapevine, designated 'G1-6819', characterized by late ripening, medium growth, with fairly good production; attractive, elongate berry shape, natural loose bunch and large berry size; holds well in cold storage and transportation; good resistance to rotting.

1 Drawing Sheet

Botanical classification/cultivar denomination: *Vitis* sp. cultivar 'G1-6819'.

BACKGROUND OF THE INVENTION

The present invention relates to a new and distinct variety of Grapevine, botanically known as *Vitis* sp., and hereinafter referred to by the name 'G1-6819'.

'G1-6819' was bred by cross pollination. The female parent was 'Bellevue' and the pollen parent was 'Centennial Seedless' (U.S. Plant Pat. No. 4,784). It has been asexually reproduced by tissue culture in South Africa. Observations made on 'G1-6819' since September 2003 have shown that the unique features of this new Grapevine are stable and reproduced true to type in successive generations.

SUMMARY OF THE INVENTION

The following traits have been repeatedly observed and are determined to be the unique characteristics of 'G1-6819'. All observations were made from specimens grown in Kern County, Calif., during September 2003. These characteristics in combination distinguish 'G1-6819' as a new and distinct Grapevine cultivar:

1. Very late ripening variety, typically ripening in September;
2. Medium growth variety, with fairly good production;
3. Nice attractive elongate berry shape, natural loose bunch and large berry size;
4. Holds well in cold storage and transportation; good resistance to rotting.

COMPARISON TO PARENT VARIETIES

The new variety differs from the female parent in the shape of the berry, with 'G1-6819' having a more elongated berry and 'Bellevue' having a more rounded berry.

The new variety differs from the male parent in color of the berry, with 'Centennial Seedless' have a more greenish berry with a tendency to discolor, while 'G1-6819' has a white creamy colored berry with no sensitivity to discoloration.

BRIEF DESCRIPTION OF ILLUSTRATIONS

The accompanying photographic illustrations show typical specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1A comprises a close-up of bunches of 'G1-6819'.

FIG. 1B comprises a close-up of the new grapevine.

DESCRIPTION OF THE NEW VARIETY

Referring now specifically to the new and distinct variety of Grapevine, the following is a detailed description of a three-year-old self-rooted vine of 'G1-6819' with color description where indicated by reference to The Royal Horticultural Society Colour Chart, except where common terms of color definition are employed.

The new variety of Grapevine as herein described may vary in slight detail due to climatic, soil and cultural conditions under which the variety may be grown, the present description being of the variety as grown at Kern County, Calif., between April and September of 2003.

Plant characteristic:

*Form.*—Upright with a moderate canopy.

*Growth.*—Moderate, vigorous growth, comparable to that of the Thompson Seedless grape, with medium canes and medium trunk.

Vegetative characteristics:

*Vine.*—Size — medium canopy with medium leaf size. Vigor — moderate. Pruning — spur pruning is sufficient due to the good fertility. Trunk — Diameter approximately 1¼ inches. Bark — Normal smooth, grey-orange color near 165A.

*Canes.*—Form — Cross-section is round to elliptic; surface is ribbed to straight. Length — from spur — average mature cane 9'–12'. Size — variety canes are fully mature at harvest time, up to 80% along the cane the brownish color showing fully maturity. Color — mature cane near 165B, grey orange group, somewhat shiny with red/burgundy dots near 183C grey-purple group. Width at center node — Cane with bunch — ½ inch; Cane without bunch — ⅝ inch. Nodes (generally) — standard node, round smooth and standard look with no deformation. No prostrate hairs and no hairs. Width at center internodes — 1 cane with bunch — ⅜ inch; 2. cane without bunch — 7/16 inch. Internodes length — Cane with bunch — 4½ inches; Cane without bunch — 5¼ inches.

*Tendrils.*—In the early stage, the spring tendrils are large and upright, at maturity the tendril break off at the splitting point; very few tendrils remain on the mature cane, three or more. Length — categorize as short — 3½ inch to the break split point and 3½ inches of curlicue, total of 7 inches for mature leaves, for green and young tendril, third from the top the length is 2½ inches to the break split point and 2½ inches of curlicue. Average Thickness — ⅜ inches. Location — mainly from the center to the top of the shoot. Leafing — no leaves grow on the tendrils. Color — mature tendrils color is grey-orange near 166C; green tendril color is yellow-green near 145A. Form — splitting into two laterals equally. Texture — straight and firm up to splitting point, splits to two equal laterals.

*Foliage.*—Density (average number of leaves about each cluster) — up to 28 leaves. The foliate of this particular variety unlike other common varieties is light due to large distance between nodes and medium leaf size. Color of immature leaf — upper side — green-yellow green near 146C. Color of mature leaf — upper side is green group near 139A; bottom side is green group color 137C. Petioles — average length, about 123 mm (shorter than main vein of the leaf); surface texture, smooth, with hairs (both erect and prostrate) absent or very sparse; anthocyanin coloration is very weak to weak. Color of petioles — light green on bright yellow background at the bottom of the petiole has small strips and/or purple dots. The petiole main color is green group color near 144A and reddish strips/or dots of red purple group color near 61B. Color of veins — bottom — yellow-green group near 145B; upper — yellow-green group near 145A. Texture of leaf surface — the leaf texture is smooth and shiny on the immature leaves; the leaf texture is smooth on both the under side and the upper side of the mature leaf, with hairs absent or very sparse. Average length of immature leaf — 4 inches. Average length of mature leaf — 5½ inches. Average width of immature leaf — 3¾ inches. Average width of mature leaf — 8 inches. Overall "shape" of leaf — serrated and rounded. Description of the leaf edge — serrated margin with two indentations approximately ⅜ inch to ½ inch in depth.

*Blooming/flowers.*—Stamens are taller than ovaries which make the flower self fertile; the position of the first flowering node is four and the number of inflorescences is, on average, 1.6 per shoot; the flower is butterfly shaped with creamy color, near 10D. Date of first bloom — Around April 20 in the south end of the San Joaquin Valley. Date of last bloom — Around May 5 in the south end of the San Joaquin Valley. Color and size of pedicel — light yellow/green, near 145B; pedicel average length is ⅛ inch. Color and size of Stamen — Yellow cream, near 5C; Stamen average length is about ⅛ inch.

*Fruit cluster.*—The bunch in general has conical shape, bunch is large, in general the bunch is semi loose. Average length, 10–12 inches; average width, 6–7¾ inches; thick strong main stem with no abscission. Point stem color at maturity on mature canes is yellow-green group near 146C. Ripening time — end of August through early September in the south end of the San Joaquin valley. Point stem color at maturity on mature canes — yellow-green group near 146C. Peduncle color at maturity — yellow-green group near 149D, 1 inch long and 3/16–¼ inch thick. Berry size — very uniform in the bunch and from bunch to bunch. Use — for fresh consumption. Keeping Quality — Good for five weeks at 33° F. Disease and pest susceptibility — Susceptible to powdery and downy mildews, although not evaluated for specific disease susceptibility; standard spraying programmer is followed in evaluation blocks to prevent disease and pest break-outs.

*Harvest time/maturity.*—First week of September through mid September. Average number of clusters per cane: 1.5. General description of the berry — elliptic shape, with a round cross-section, medium bloom, slightly firm, with neutral flavor. The berries are well attached to the cap. The variety has very little shatter and berries separate easily from the pedicel. Average size of the berry (no Gibberelic acid) — length approximately 24.9 mm, width approximately 18.4 mm. Average size of the berry (with 10 ppm Gibberelic acid) — length approximately 30.1 mm, width approximately 21.0 mm. Average berry weight of untreated vine without Gibberelic acid — 4.5 gr. Average bunch weight (no Gibberelic acid) — approximately 18 ounces. Average bunch weight (with 10 ppm Gibberelic acid) — approximately 34 ounces. Average brix (no Gibberelic acid) — approximately 17–18. Average brix (with 10 ppm Gibberelic acid) — approximately 15–16. Set of the berry — average natural shatter. Skin of berry — semi shiny smooth surface, slightly tougher than Thompson Seedless; completely resistant to discoloration or brown browsing, somewhat sensitive to cracking (between about 5% to 7%). Skin thickness — skin thickness — fruit thickness slightly thicker than Thompson Seedless. Color of skin — creamy green color — yellow-green group near 146C. Color of pulp — clear white crystal clear. Texture of berry pulp — meaty from one side and juicy from other side. Presence of seeds — no seed trace.

We claim:

1. A new and distinct variety of *Vitis* sp. plant, identified as 'G1-6819', substantially as shown and described.

* * * * *

FIG 1A
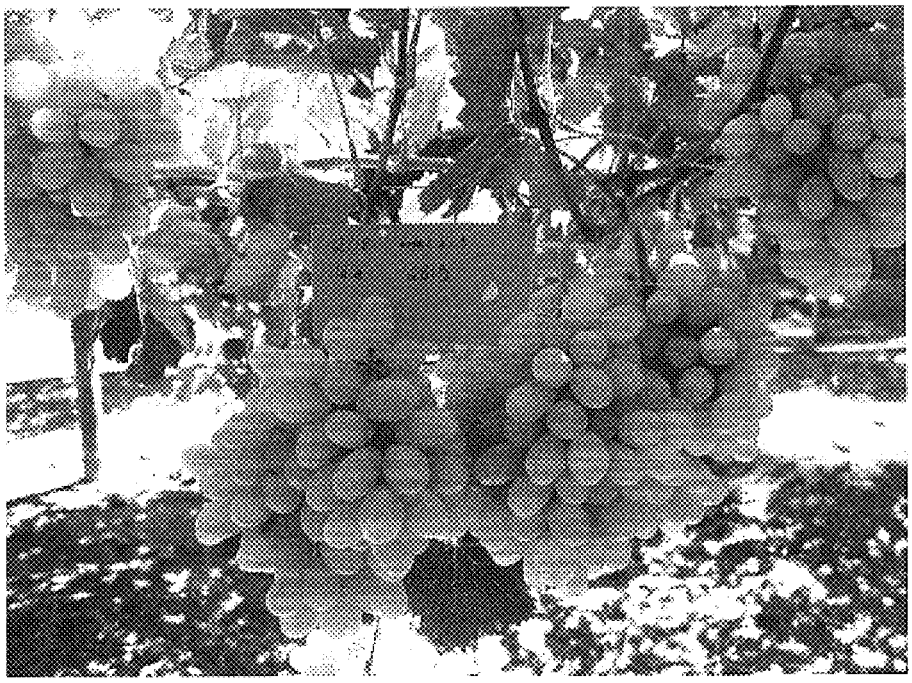
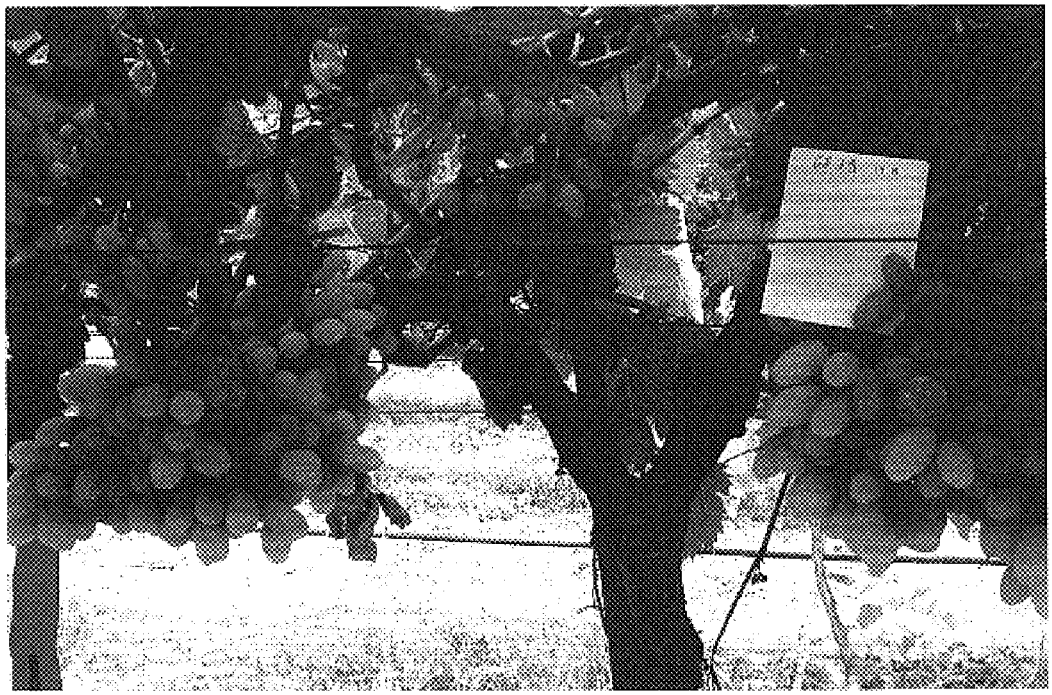
FIG 1B